United States Patent
Liu et al.

(10) Patent No.: US 8,034,533 B2
(45) Date of Patent: Oct. 11, 2011

(54) FLUORINE-FREE HETEROAROMATIC PHOTOACID GENERATORS AND PHOTORESIST COMPOSITIONS CONTAINING THE SAME

(75) Inventors: Sen Liu, Highland Park, NJ (US); Pushkara R. Varanasi, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 872 days.

(21) Appl. No.: 12/015,047

(22) Filed: Jan. 16, 2008

(65) Prior Publication Data

US 2009/0181320 A1 Jul. 16, 2009

(51) Int. Cl.
G03F 7/028 (2006.01)
G03F 7/26 (2006.01)
C07C 309/04 (2006.01)
C07C 309/06 (2006.01)

(52) U.S. Cl. .............. 430/270.1; 430/313; 430/921; 430/922; 562/30

(58) Field of Classification Search ........ 430/270.1, 430/326, 921, 922, 313; 544/146; 562/30
See application file for complete search history.

(56) References Cited

U.S. PATENT DOCUMENTS

| | | | |
|---|---|---|---|
| 4,855,017 A | | 8/1989 | Douglas |
| 5,229,254 A | * | 7/1993 | Lohaus et al. .......... 430/281.1 |
| 5,362,663 A | | 11/1994 | Bronner et al. |
| 5,429,710 A | | 7/1995 | Akiba et al. |
| 5,558,978 A | * | 9/1996 | Sch adeli et al. ........ 430/270.1 |
| 5,562,801 A | | 10/1996 | Nulty |
| 5,618,751 A | | 4/1997 | Golden et al. |
| 5,744,376 A | | 4/1998 | Chan et al. |
| 5,801,094 A | | 9/1998 | Yew et al. |
| 5,821,469 A | | 10/1998 | Shanmugham |
| 5,948,570 A | | 9/1999 | Kornblit et al. |
| 6,203,965 B1 | | 3/2001 | Cameron et al. |
| 6,436,606 B1 | * | 8/2002 | Hatakeyama et al. ..... 430/270.1 |
| 6,627,391 B1 | | 9/2003 | Ito et al. |
| 6,635,401 B2 | | 10/2003 | Li et al. |
| 6,730,452 B2 | | 5/2004 | Brock et al. |
| 6,756,180 B2 | | 6/2004 | Li et al. |
| 6,811,961 B2 | | 11/2004 | Cameron et al. |
| 6,902,874 B2 | | 6/2005 | Li et al. |
| 7,026,093 B2 | | 4/2006 | Thackeray et al. |
| 7,063,931 B2 | | 6/2006 | Li et al. |
| 7,087,356 B2 | | 8/2006 | Khojasteh et al. |
| 7,192,686 B2 | | 3/2007 | Meagley |
| 2003/0008230 A1 | | 1/2003 | Li et al. |
| 2005/0158654 A1 | | 7/2005 | Yuch et al. |
| 2005/0277755 A1 | | 12/2005 | Hamada et al. |
| 2006/0188810 A1 | | 8/2006 | Ohsawa et al. |
| 2006/0216643 A1 | | 9/2006 | Li et al. |
| 2007/0172769 A1 | | 7/2007 | Kanna et al. |
| 2009/0176173 A1 | * | 7/2009 | Glodde et al. .......... 430/281.1 |

OTHER PUBLICATIONS

Hiroshi Ito; Chemical Amplification resists for microlithography—Adv. Polym. Sci. (2005) 172; pp. 37-245.
Everyscience—Glossary-E; http://www.everyscience.com/Chemistry/Glossary/E.php—pp. 1-3, Dec. 7, 2007.
Yasuhiro Suzuke, et al.; Photoacid Generators in Chemically Amplified Resists—SPIE vol. 3333 (1998)—pp. 735-746.
Ramakrishnan Ayothi, et al.; All-Organic Non-PFOS Nonionic Photoacid Generating Compounds With Functionalized Fluoroorganic Sulfonate Motif for Chemically Amplified Resists—Proc. of SPIE vol. 6153, 61530J, (2006) pp. 61530J-1-61530J-7.
Ramakrishnan Ayothi, et al.; New PFOS Free Photoresist Systems for EUV Lithography—Journal of Photopolymer Science and Technology, vol. 19, No. 4 (2006) pp. 515-520.
Kyung-Min Kim, et al.; Synthesis, Characterization and Lithography Performance of Phtotacid Generator With Short Perfluoroalkyl Anion—Polymer Bulletin 55, (2005) pp. 333-340.
E. Reichmanis, et al.; Chemical Amplification Mechanisms for Microlithography—American Chemical Society; Chem. Mater. 1991, 3, pp. 394-407.
James V. Crivello; The Discovery and Development of Onium Salt Cationic Photoinitiators—Journal of Polymer Science; Part A; Polymer Chemistry, vol. 37, (1999), pp. 4241-4254.
Mingxing Wang, et al.; Novel Polymeric Anionic Photoacid Generators (PAGs) and Photoresists for Sub-100 nm Patterning by 193 nm Lithography—Advances in Resist Materials and Processing Technology XXIV, edited by Qinghuang Lin—Proc. of SPIE vol. 6519, 6519C, (2007).
Mary Kate Boggiano, et al.; Photoresists for CO2-Based Next-Generation Microlithography—Advances in Resist Technology and Processing XXII, Edited by John L. Sturtevant—Proc. of SPIE vol. 5753 (SPIE, Bellingham, WA, 2005) pp. 487-490.
International Search Report and WO-PCT/US2009/030789 Inter'l filing date: Jan. 13, 2009.

* cited by examiner

Primary Examiner — Cynthia Kelly
Assistant Examiner — Anca Eoff
(74) Attorney, Agent, or Firm — Yuanmin Cai

(57) ABSTRACT

Fluorine-free photoacid generators and photoresist compositions containing fluorine-free photoacid generators are enabled as alternatives to PFOS/PFAS photoacid generator-containing photoresists. The photoacid generators are characterized by the presence of a fluorine-free heteroaromatic sulfonate anionic component. The photoacid generators preferably contain an onium cationic component, more preferably a sulfonium cationic component. The photoresist compositions preferably contain an acid sensitive imaging polymer. The compositions are especially useful for forming material patterns using 193 nm (ArF) imaging radiation.

17 Claims, No Drawings

FLUORINE-FREE HETEROAROMATIC PHOTOACID GENERATORS AND PHOTORESIST COMPOSITIONS CONTAINING THE SAME

BACKGROUND OF THE INVENTION

In the field of semiconductor manufacturing, optical lithography has been the mainstream approach used in patterning semiconductor devices. In typical prior art lithography processes, UV light is projected onto a silicon wafer coated with a thin layer of photosensitive resist (photoresist) through a mask that defines a particular circuitry pattern. Exposure to UV light, followed by subsequent baking, induces a photochemical reaction which changes the solubility of the exposed regions of the photoresist. Thereafter, an appropriate developer, usually an aqueous base solution, is used to selectively remove photoresist either in the exposed regions (positive-tone photoresists) or, in the unexposed regions (negative-tone photoresists). The pattern thus defined is then imprinted on the silicon wafer by etching away the regions that are not protected by the photoresist with a dry or wet etch process.

One type of photoresist employed in the prior art is a chemically amplified photoresist which uses acid catalysis. A typical prior art chemically amplified photoresist, for example, is formulated by dissolving an acid sensitive polymer and a photoacid generator in a casting solution. A chemically amplified photoresist is especially useful when relatively short wavelength radiation is employed, including deep UV radiation 150-315 nm wavelengths, and mid-UV radiation, e.g., 350-450 nm wavelengths. The shorter wavelengths are typically desired to increase resolution, and thus, decrease feature size of the semiconductor devices, but fewer photons are radiated for a given energy dose.

Accordingly, higher exposure doses are typically required when using UV radiation to obtain a sufficient photochemical response in the photoresist unless a chemically amplified photoresist is employed. In a chemically amplified photoresist, acid sensitivity of the base polymer exists because acid sensitive side chain groups are bonded to the polymer backbone. When such a photoresist is exposed to radiation, the photoacid generator produces an acid that, when the photoresist is heated, causes catalytic cleavage of the acid sensitive side chain groups. A single acid catalyst molecule generated in this manner may be capable of cleaving multiple side chain groups, thus allowing lower exposure doses for the needed photochemical response.

Because of the relatively low intensity of ArF laser source and relatively high binding energy of acid labile moieties in ArF photoresist, photoacid generators which can produce stronger Bronsted acid with much higher sensitivity are preferred to realize such chemical amplification in commercial lithography. Fluorine-containing onium salts, such as perfluoronated octyl sulfonate (PFOS) and perfluoronated alkyl sulfonate (PFAS), are generally preferred used as the photoacid generator in ArF photoresist system in part because they result in generation of strong acid.

In recent years, there has been a desire in the microelectronics industry to eliminate the use of perfluorinated carbons (PFCs) such as PFOS and PFAS. Thus, there is a desire to find alternative photoacid generators which can be used without adversely impacting the performance of lithographic processes. There has also been a desire to minimize or eliminate fluorine content in photoresist in order to improve etch resistance and to improve process latitude in high numeric aperture (NA>0.95) imaging processes.

Some attempts have been made to develop photoresist formulations that do not use perfluorinated carbon-containing photoacid generators, however these have largely been unsuccessful in achieving performance comparable to formulations using PFOS. Thus, there is a need for new and improved photoacid generators and chemically amplified photoresist compositions that enable the substantial reduction or avoidance of PFCs and/or fluorine in photoresist compositions.

SUMMARY OF THE INVENTION

The invention provides fluorine-free photoacid generators and photoresist compositions comprising fluorine-free photoacid generators. The photoacid generators of the invention provide a viable alternative to the PFC-containing photoacid generators currently used in the industry. The invention also provides photoresist compositions containing fluorine-free photoacid generators that show excellent optical clarity, thermal stability and lithographic performance (photospeed comparable with photoresists using of the commercial PFC-containing photoacid generators).

In one aspect, the invention encompasses fluorine-free photoacid generators comprising an onium cationic component and an anionic component having the structure:

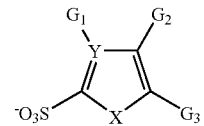

wherein:

X is selected from the group consisting of S, O and NR,

R is selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;

Y is selected from the group consisting of C and N; and each of $G_1$-$G_3$ is selected from the group consisting of R and an electron withdrawing moiety, provided that when Y is N, $G_1$ is not present in the structure.

The cationic component is preferably a sulfonium cation. The cationic component preferably includes an aromatic moiety.

In another aspect, the invention encompasses photoresist compositions containing an acid sensitive imaging polymer and a fluorine-free photoacid generator of the invention. Preferably, the imaging polymer includes a lactone moiety.

The invention also encompasses processes for using the compositions of the invention to form patterned material structures on a substrate. These methods preferably involve the use of 193 nm (ArF) imaging radiation.

These and other aspects of the invention are described in further detail below.

DETAILED DESCRIPTION OF THE INVENTION

The invention provides fluorine-free photoacid generators. The photoacid generators of the invention provide a viable alternative to the PFC-containing photoacid generators currently used in the industry. The invention also provides photoresist compositions containing fluorine-free photoacid generators that show excellent optical clarity, thermal stability and lithographic performance (photospeed comparable with photoresists using of the commercial PFC-containing photoacid generators).

In one aspect, the fluorine-free photoacid generators of the invention are characterized by the presence of an onium cationic component and an anionic component having the structure:

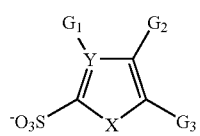
(I)

wherein:
X is selected from the group consisting of S, O and NR,
R is selected from the group consisting of H; linear, branched, tertiary, or cyclic alkyl (preferably $C_1$-$C_{12}$ or $C_4$-$C_{12}$ in the case or tertiary and cyclic); linear, branched, tertiary or cyclic alkoxyl (preferably $C_1$-$C_{12}$ or $C_4$-$C_{12}$ in the case or tertiary and cyclic); unsubstituted and substituted phenyl; unsubstituted and substituted naphthyl; or unsubstituted and substituted fluorenyl;
Y is selected from the group consisting of C and N; and
each of $G_1$-$G_3$ is selected from the group consisting of R and an electron withdrawing moiety, provided that when Y is N, $G_1$ is not present in the structure.

Preferred cationic components have the formula $Q_nZ^+$ where: Z is selected from sulfur and iodine, n is 3 when Z is sulfur and 2 when Z is iodine, and at least one of Q comprises an aromatic moiety. Two preferred cation structures are:

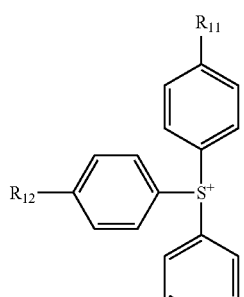
(II)

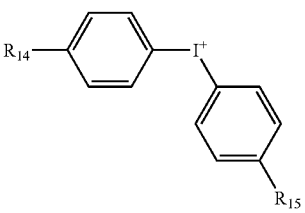
(III)

where $R_{11}$, $R_{12}$, $R_{13}$, $R_{14}$, and $R_{15}$ are independently selected from the group consisting of H; linear, branched, tertiary, or cyclic alkyl (preferably $C_1$-$C_{12}$ or $C_4$-$C_{12}$ in the case or tertiary and cyclic); linear, branched, tertiary or cyclic alkoxyl (preferably $C_1$-$C_{12}$ or $C_4$-$C_{12}$ in the case or tertiary and cyclic); unsubstituted and substituted phenyl; unsubstituted and substituted naphthyl; or unsubstituted and substituted fluorenyl. An example of an iodonium cation of this structure is:

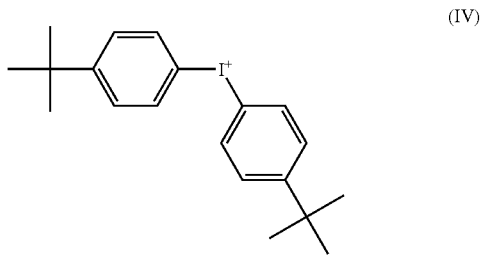
(IV)

Another preferred cation structure is:

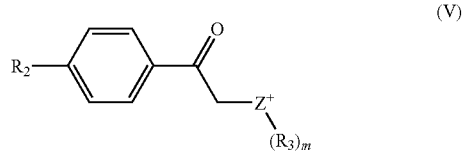
(V)

where each $R_2$ is independently selected from the group consisting of H; linear, branched, tertiary, or cyclic alkyl (preferably $C_1$-$C_{12}$ or $C_4$-$C_{12}$ in the case or tertiary and cyclic); linear, branched, tertiary or cyclic alkoxyl (preferably $C_1$-$C_{12}$ or $C_4$-$C_{12}$ in the case or tertiary and cyclic); unsubstituted and substituted phenyl; unsubstituted and substituted naphthyl; or unsubstituted and substituted fluorenyl; Z is selected from sulfur and iodine, m is 2 when Z is sulfur and 1 when Z is iodine; and each $R_3$ is independently selected from the group consisting of H; linear, branched, tertiary, or cyclic alkyl (preferably $C_1$-$C_{12}$ or $C_4$-$C_{12}$ in the case or tertiary and cyclic); linear, branched, tertiary or cyclic alkoxyl (preferably $C_1$-$C_{12}$ or $C_4$-$C_{12}$ in the case or tertiary and cyclic); unsubstituted and substituted phenyl; unsubstituted and substituted naphthyl; or unsubstituted and substituted fluorenyl; or $R_3$ is collectively an alkylene $(CH_2)_n$ chain (preferably $C_2$-$C_{12}$).

Examples of the anionic component of structure (I) are:

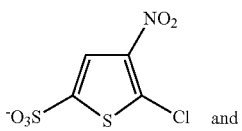
(VI)

and

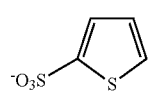
(VII)

The invention is not limited to any specific method for synthesizing the photoacid generators of the invention. One possible synthesis route is shown in Scheme 1 below. In this scheme, photoacid generators of the invention can be made in a one-pot reaction from sulfonyl chloride to its corresponding silver sulfonate without the intermediate sulfuric acid. The heteroaromatic sulfonyl chloride reacted with silver carbonate to afford the silver salt in solid phase at almost quantitative yield. The resulting silver salt may then be reacted with corresponding sulfonium or iodonium source to afford the desirable photoacid generator. The chemical structures of the resulting compounds can be confirmed by their $^1$H NMR spectra.

Scheme 1. Synthesis of Hetero-Aromatic Photoacid Generators (PAGs).

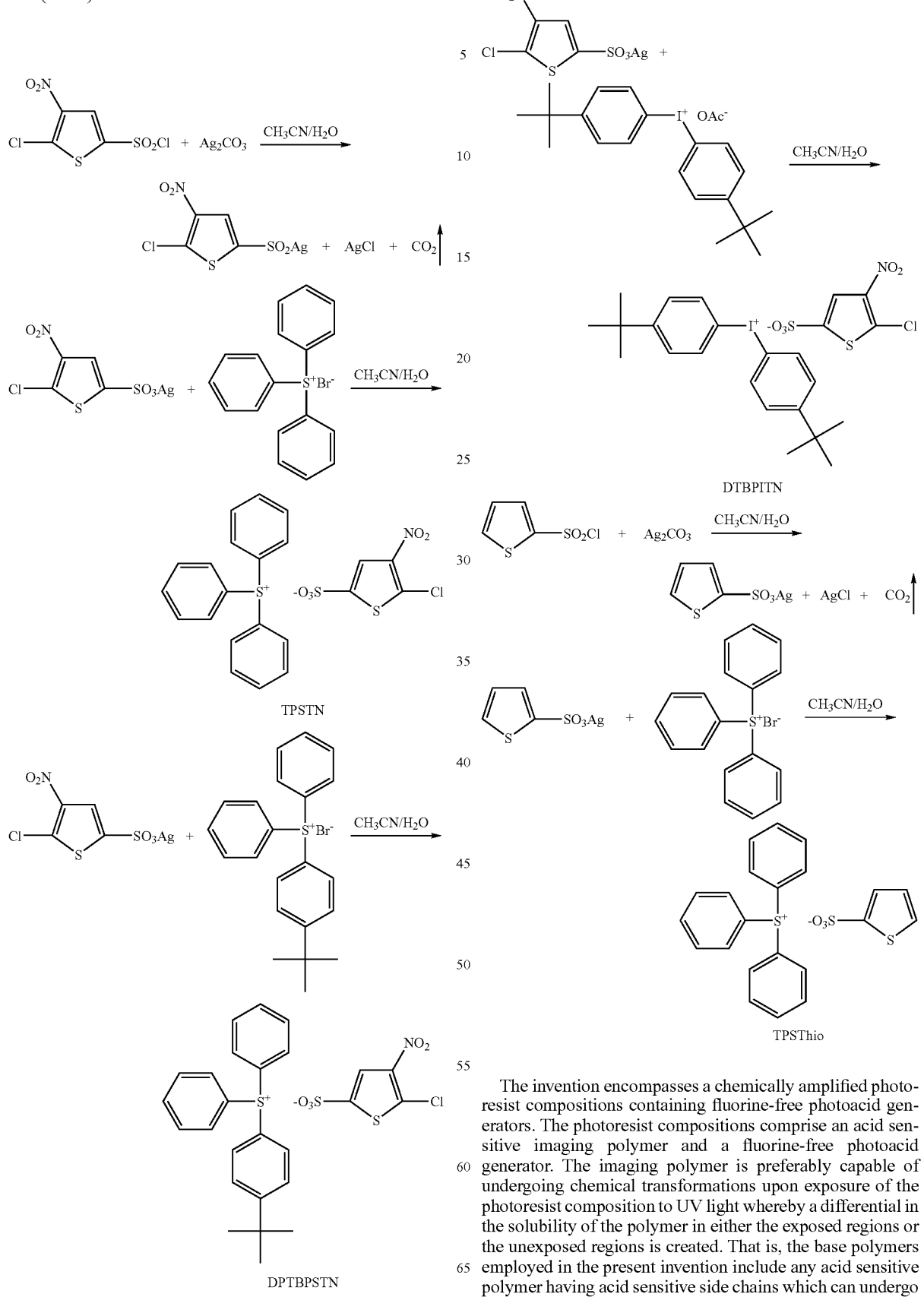

The invention encompasses a chemically amplified photoresist compositions containing fluorine-free photoacid generators. The photoresist compositions comprise an acid sensitive imaging polymer and a fluorine-free photoacid generator. The imaging polymer is preferably capable of undergoing chemical transformations upon exposure of the photoresist composition to UV light whereby a differential in the solubility of the polymer in either the exposed regions or the unexposed regions is created. That is, the base polymers employed in the present invention include any acid sensitive polymer having acid sensitive side chains which can undergo catalytic cleavage in the presence of an acid generated by the inventive photoacid generator. The imaging polymer may be either a positive-tone imaging polymer or a negative-tone imaging polymer. In such polymers, the acid sensitivity exists because of the presence of acid sensitive side chains that are bonded to the polymer backbone. Such acid sensitive polymers including acid sensitive side chains are conventional and are well known in the art. Preferably, the imaging polymer is one suitable for use in 193 nm (ArF) lithography.

In some embodiments, the acid sensitive side chains of the acid sensitive polymers are protected with various acid labile protecting groups that are well known to those skilled in the art. For example, the acid sensitive side chains may be protected with high activation energy protecting groups such as t-butyl ester or t-butyl carbonyl groups, a low activation energy protecting group such as acetal, ketal, or silyethers, or a combination of both low and high activation energy protecting groups may also be used. The imaging polymer of the invention contains a lactone moiety, more preferably a pendant lactone moiety. Examples of imaging polymers containing lactone moieties are well known in the art. See for example US Published Patent Application No. 20060216643A1, and U.S. Pat. Nos. 7,087,356, 7,063,931, 6,902,874, 6,730,452, 6,627,391, 6,635,401 and 6,756,180. Some preferred lactone-containing monomeric units for inclusion in the imaging polymer are:

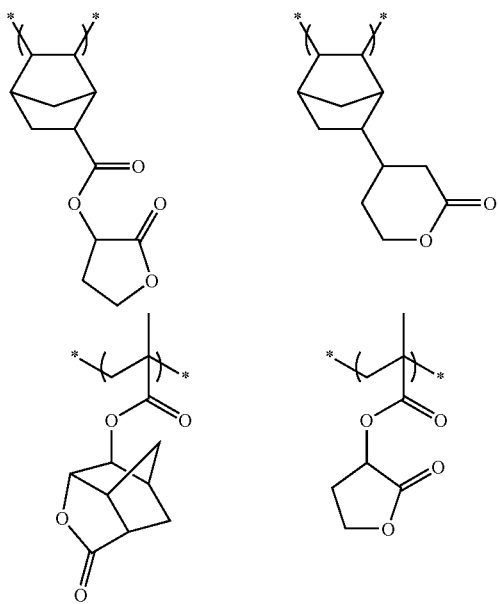

Preferred imaging polymers contain at least about 5 mole % of lactone-containing monomeric units based on the total monomeric units in the imaging polymer, more preferably about 10-50 mole %, most preferably 15-35 mole %.

The photoresist compositions of the invention preferably contain a solvent which is capable of dissolving the acid sensitive polymer. Illustrative examples of such solvents include, but are not limited to: ethers, glycol ethers, aromatic hydrocarbons, ketones, esters and the like. A solvent system including a mixture of the aforementioned solvents is also contemplated herein. Suitable glycol ethers include: 2-methoxyethyl ether (diglyme), ethylene glycol monomethyl ether, propylene glycol monomethyl ether, propylene glycol monomethylether acetate (PGMEA) and the like. Examples of suitable aromatic hydrocarbon solvents that include: toluene, xylene, and benzene. Examples of ketones include: methylisobutylketone, 2-heptanone, cycloheptanone, and cyclohexanone. An example of an ether solvent is tetrahydrofuran, whereas ethyl lactate and ethoxy ethyl propionate are examples of ester solvents that may be employed herein. PGMEA is a preferred solvent.

In addition to the above components, the photoresist composition may also include other components such as photosensitizers, bases, surfactants or other additives. If desired, combinations or mixtures of these other components may be used (e.g., a photosensitizer and a base).

The optional photosensitizer is preferably one containing chromophores that are capable of absorbing irradiation in 193 nm (ArF) lithography. Illustrative examples of such compounds include, but are not limited to: 9-anthracene methanol, coumarins, 9,10-bis(trimethoxysilyethynyl) anthracene and polymers containing these chromophores. Of these compounds, it is highly preferred to use 9-anthracene methanol as the photosensitizer.

The optional bases that can be employed in the present invention include, but are not limited to: berberine, cetyltrimethylammonium hydroxide, 1,8-bis(dimethylamino)naphthalene, tetrabutyl ammonium hydroxide (TBAH), amines, polymeric amines and the like. When a base is employed with the inventive chemically amplified photoresist composition, it is highly preferred to use TBAH as the base.

The optional surfactants that can be employed in the photoresist compositions include any surfactant that is capable of improving the coating homogeneity of the chemically amplified photoresist composition of the present invention. Illustrative examples include: fluorine-containing surfactants such as 3M's FC-430® and siloxane-containing surfactants such as Union Carbide's Silwet® series.

The photoresist compositions of the invention preferably comprise from about 5 to about 30 weight % imaging polymer, from about 50 to about 94.9 weight % solvent, and from about 0.1 to about 20 weight % fluorine-free photoacid generator (the weight % fluorine-free photoacid generator being based on the total weight of imaging polymer present in the composition). When a photosensitizer is employed, it is preferably present in an amount of from about 0.001 to about 8 weight %, based on the total weight of imaging polymer. If a base is employed, the optional base is preferably present in an amount of from about 0.1 to about 1 weight %, based on the total weight of imaging polymer. When a surfactant is employed, it is preferably present in amount of from about 0.001 to about 0.1 weight %, based on the total weight of imaging polymer.

More preferably, the photoresist composition comprises from about 10 to about 20 weight % of imaging polymer, from about 80 to about 90 weight % solvent, and from about 1 to about 5 weight % of fluorine-free photoacid generator (based on the total weight of imaging polymer present in the composition) optionally, from about 0.01 to about 5 weight % photosensitizer, based on the total weight of imaging polymer, optionally, from about 0.1 to about 0.5 weight % base, based on the total weight of imaging polymer, and optionally, from about 0.001 to about 0.01 weight % surfactant, based on the total weight of imaging polymer.

Note that the amounts given above are exemplary and that other amounts of each of the above components, which are typically employed in the photolithography industry, can also be employed herein.

The invention also encompasses processes for using the compositions of the invention to form patterned material features on a substrate. These methods preferably involve the use of 193 nm (ArF) imaging radiation. The methods of the invention preferably comprise:

(a) providing a material surface on a substrate,
(b) forming a photoresist layer over the material surface, the photoresist being a photoresist of the invention,
(c) patternwise exposing said photoresist layer to radiation thereby creating a pattern of radiation-exposed regions in said photoresist layer,
(d) selectively removing portions of said photoresist layer to expose portions of said material surface, and
(e) etching or ion implanting said exposed portions of said material, thereby forming said patterned material feature.

The material surface of the substrate may be a metal conductor layer, a ceramic insulator layer, a semiconductor layer or other material depending on the stage of the manufacture process and the desired material set for the end product. The compositions of the invention are especially useful for lithographic processes used in the manufacture of integrated circuits on semiconductor substrates. The compositions of the invention in lithographic processes to create patterned material layer structures such as metal wiring lines, holes for contacts or vias, insulation sections (e.g., damascene trenches or shallow trench isolation), trenches for capacitor structures, ion implanted semiconductor structures for transistors, etc. as might be used in integrated circuit devices.

In some cases, a bottom antireflective coating and/or underlayer coating (e.g., a planarizing underlayer) may be applied between the photoresist layer and the material surface. In some cases, a top antireflective coating layer may be applied over the photoresist layer (i.e., on the side of the photoresist layer distal from the material surface). The invention is not limited to the use of antireflective reflective coatings and/or underlayer materials, nor specific compositions of those coatings or materials.

The photoresist layer is then patternwise-exposed to the desired radiation (e.g. 193 nm ultraviolet radiation). The patternwise exposure is conducted through a mask which is placed over the photoresist layer. For 193 nm UV radiation, the total exposure energy is preferably about 100 millijoules/cm$^2$ or less, more preferably about 50 millijoules/cm$^2$ or less (e.g. 15-30 millijoules/cm$^2$).

After the desired patternwise exposure, the photoresist layer is typically baked to further complete the acid-catalyzed reaction and to enhance the contrast of the exposed pattern. The post-exposure bake is preferably conducted at about 60-175° C., more preferably about 90-160° C. The post-exposure bake is preferably conducted for about 30 seconds to 5 minutes.

After post-exposure bake, if any, the photoresist structure with the desired pattern is obtained (developed) by contacting the photoresist layer with an aqueous alkaline solution which selectively dissolves the areas of the photoresist which were exposed to radiation in the case of a positive photoresist (or the unexposed areas in the case of a negative photoresist). Preferred aqueous alkaline solutions (developers) are aqueous solutions of tetramethyl ammonium hydroxide. The resulting lithographic structure on the substrate is then typically dried to remove any remaining developer. If a top antireflective coating has been used, it is preferably also dissolved by the developer in this step.

The pattern from the photoresist structure may then be transferred to the exposed portions of underlying material of the substrate by etching with a suitable etchant using techniques known in the art; preferably the transfer is done by reactive ion etching or by wet etching. Once the desired pattern transfer has taken place, any remaining photoresist may be removed using conventional stripping techniques. Alternatively, the pattern may be transferred by ion implantation to form a pattern of ion implanted material.

Examples of general lithographic processes where the composition of the invention may be useful are disclosed in U.S. Pat. Nos. 4,855,017; 5,362,663; 5,429,710; 5,562,801; 5,618,751; 5,744,376; 5,801,094; 5,821,469 and 5,948,570. Other examples of pattern transfer processes are described in Chapters 12 and 13 of "Semiconductor Lithography, Principles, Practices, and Materials" by Wayne Moreau, Plenum Press, (1988). It should be understood that the invention is not limited to any specific lithography technique or device structure.

The invention is further described by the examples below. The invention is not limited to the specific details of the examples.

EXAMPLES

Example 1

Synthesis of Silver 5-chloro-4-nitrothiophene-2-sulfonate

To a solution of 5-chloro-4-nitrothiophene-2-sulfonyl chloride (0.393 g, 1.5 mmol) in 15 mL of acetonitrile and 2 mL of water was added silver carbonate (0.414 g, 1.5 mmol) in portions in darkness. The resulting suspension was stirred overnight for 3 days, until no starting material is shown on the thin layer chromatography with an eluant of hexane/ethyl acetate (1:4). The mixture was filtered through half an inch of Celite® and the solid was washed with 3×15 mL acetonitrile. The organic filtrate was combined and organic solvent was removed via rotary evaporator to dryness and thus afforded 0.507 g of viscous solid with a yield of 96.4%. The resulting compound was not purified for further reactions. $^1$HNMR, d6-DMSO: 7.49 (d, 1H, 0.8 Hz)

Example 2

Synthesis of Triphenyl Sulfonium 5-chloro-4-nitrothiophene-2-sulfonate. (TPSTN)

To a solution of silver 5-chloro-4-nitrothiophene-2-sulfonate (0.25 g, 0.713 mmol) in 15 mL of acetonitrile was added a solution of triphenyl sulfonium bromide (1.373 g, 4 mmol) in 10 mL of acetonitrile and 1 mL of water. The resulting mixture was stirred overnight for 3 days and the solid was allowed to precipitate for 1 day before it was filtered. The organic solvent was removed via rotary evaporator and the residue was re-dissolved in 30 mL of 2-butanone. The resulting solution was washed with 3×5 mL of water, dried over magnesium sulfate and filtered though Celite® and aluminum oxide basic. The organic solvent wad removed via rotary evaporator and dried over vacuum oven to dryness and thus afforded 0.306 g of product with a yield of 85%. $^1$HNMR, d6-DMSO: 7.90-7.75 (m, 15H), 7.48 (s, 1H). DSC (10° C./min, nitrogen 5 mL/min) showed no obvious decomposition up to 250° C.

Example 3

Synthesis of tert-butylphenyldiphenyl sulfonium 5-chloro-4-nitrothiophene-2-sulfonate. (DPTBPSTN)

To a solution of silver 5-chloro-4-nitrothiophene-2-sulfonate (0.631 g, 1.8 mmol) in 40 mL of acetonitrile and 2 mL of water was added a solution of tert-butylphenyldiphenyl sulfonium bromide (0.759 g, 1.8 mmol) in 20 mL of acetonitrile and 2 mL of water. The resulting mixture was stirred overnight for 5 days before it was filtered. The organic solvent was removed via rotary evaporator and the residue was re-dissolved in 60 mL of 2-butanone. The resulting solution was washed with 3×10 mL of water, dried over magnesium sulfate and filtered though Celite® and aluminum oxide basic. The organic solvent wad removed via rotary evaporator and dried over vacuum oven to dryness and thus afforded 1.06 g of product with a yield of 92%. $^1$HNMR, d6-DMSO: 7.87-7.75 (m, 14H), 7.48 (s, 1H), 1.32 (s, 9H). DSC (10° C./min, nitrogen 5 mL/min) showed no obvious decomposition up to 250° C.

Example 4

Synthesis of Di(tert-butylphenyl) iodonium 5-chloro-4-nitrothiophene-2-sulfonate. (DTBPITN)

To a solution of silver 5-chloro-4-nitrothiophene-2-sulfonate (0.631 g, 1.8 mmol) in 40 mL of acetonitrile and 2 mL of water was added a solution of di(tert-butylphenyl) iodonium acetate (0.814 g, 1.8 mmol) in 20 mL of acetonitrile and 2 mL of water. The resulting mixture was stirred overnight for 5 days before it was filtered and the solid was washed by 60 mL of acetonitrile. The organic solvent was removed via rotary evaporator and the residue was re-dissolved in 200 mL of 2-butanone. The resulting solution was filtered through though Celite® and aluminum oxide basic. The organic solvent wad removed via rotary evaporator and dried over vacuum oven to dryness and thus afforded 1.0 g of product with a yield of 87%. $^1$HNMR, d6-DMSO: 8.15 (d, 8.8 Hz, 4H), 7.54 (d, 8.8 Hz, 4H), 7.49 (s, 1H), 1.26 (s, 18H). DSC (10° C./min, nitrogen 5 mL/min): Td, 167° C.

Example 5

Synthesis of Triphenyl Sulfonium thiophene-2-sulfonate (TPSThio)

To a solution of thiophene-2-sulfonyl chloride (0.913 g, 5 mmol) in 40 mL of acetonitrile and 1 mL of water was added silver carbonate (1.38 g, 5 mmol) in portions in darkness. The resulting suspension was stirred overnight for 3 days, until no starting material is shown on the thin layer chromatography with an eluant of hexane/ethyl acetate (1:4). The mixture was filtered through half an inch of Celite® and the solid was washed with 3×15 mL acetonitrile. The organic filtrate was combined and organic solvent was removed via rotary evaporator to dryness.

The resulting silver thiophene-2-sulfonate was re-dissolved in 40 mL of acetonitrile and 1 mL of water. To this solution was added a solution of triphenyl sulfonium bromide (1.716 g, 5 mmol) iodonium acetate (0.814 g, 1.8 mmol) in 10 mL of acetonitrile and 1 mL of water. The resulting mixture was stirred overnight for 3 days before it was filtered and the solid was washed by 50 mL of acetonitrile. The organic solvent was removed via rotary evaporator and the residue was washed by 3×5 mL of water and re-dissolved in 50 mL of 2-butanone. The resulting solution was dried over magnesium sulfate and filtered through Celite® and basic aluminum oxide. The organic solvent was removed via rotary evaporator and dried over vacuum oven to dryness and thus afforded 1.70 g of product with a yield of 80%. $^1$HNMR, d6-DMSO: 7.90-7.75 (m, 15H), 7.40 (dd, 4.8 Hz, 0.6 Hz, 1H), 7.10 (dd, 2.7 Hz, 0.6 Hz, 1H), 6.89 (4.8 Hz, 2.7 Hz, 1H), DSC (10° C./min, nitrogen 5 mL/min) showed no obvious decomposition up to 250° C.

Example 6

Synthesis of 1-(2-oxo-2-p-tolyl-ethyl)-tetrahydro-thiophenium bromide

To a solution of 2-bromo-4'-methylacetophenone (19.18 g, 90 mmol) in 120 mL of acetone and 4.9 mL of water at 0° C. was added tetrahydrothiophene (15.87 g, 180 mmol) dropwise. The resulting mixture was stirred at 0° C. for 1 hour before solid precipitated and was then stirred at room temperature for 1 hour. The resulting crude product was filtered through glass frit as solid and was washed by 100 mL of cold acetone. The crude product was recrystallized by 150 mL of ethanol to afford 19.8 g pure product at a yield of 73%. $^1$HNMR, d6-DMSO: 7.92 (d, 8.0 Hz, 2H), 7.43 (d, 8.0 Hz, 2H), 5.39 (s, 2H), 3.57 (m, 4H), 2.42 (s, 3H), 2.27 (m, 2H), 2.19 (m, 2H).

Example 7

Synthesis of 1-(2-oxo-2-p-tolyl-ethyl)-tetrahydro-thiophenium 5-chloro-4-nitrothiophene-2-sulfonate (BTN)

To a solution of silver 5-chloro-4-nitrothiophene-2-sulfonate (0.6 g, 1.71 mmol) in 30 mL of acetonitrile was added a solution of 1-(2-oxo-2-p-tolyl-ethyl)-tetrahydro-thiophenium bromide (0.516 g, 1.71 mmol) in 20 mL of acetonitrile and 2 mL of water. The resulting mixture was stirred overnight for 3 days before it was filtered through Celite® and the remaining solid was washed by 50 mL of acetonitrile. The organic solvent was then removed via rotary evaporator and the residue was taken by 100 mL of 2-butanone. The resulting solution was then dried over magnesium sulfate, filtered though Celite® and basic aluminum oxide, concentrated via rotary evaporator, dried over vacuum oven to dryness and thus afforded 0.5 g of product at a yield of 63%. $^1$HNMR, d6-DMSO: 7.90 (d, 8.4 Hz, 2H), 7.48 (s, 1H), 7.44 (d, 8.0 Hz, 2H), 5.29 (s, 2H), 3.63-3.55 (m, 2H), 3.55-3.46 (m, 2H), 2.42 (s, 3H), 2.35-2.13 (brm, 4H), DSC (10° C./min, nitrogen 5 mL/min): Td, 218° C.

Example 8

Synthesis of 1-(2-naphthalen-2-yl-2-oxo-ethyl)-tetrahydro-thiophenium Bromide

To a solution of 2-bromo-2'-acetonaphthone (18.68 g, 75 mmol) in 100 mL of acetone and 4.1 mL of water at 0° C. was added tetrahydrothiophene (13.23 g, 150 mmol) dropwise. The resulting mixture was stirred at 0° C. for 1 hour before solid precipitated and was then stirred at room temperature for 1 hour. The resulting crude product was filtered through glass frit as solid and was washed by 100 mL of cold acetone. The crude product was recrystallized by 150 mL of ethanol to afford 19.0 g pure product at a yield of 75%. $^1$HNMR, d6-DMSO: 8.82 (s, 1H), 8.17-7.98 (m, 4H), 7.78-7.65 (m, 2H), 5.63 (s, 2H), 3.64 (m, 4H), 2.40-2.29 (brm, 2h), 2.28-2.17 (brm, 2H).

Example 9

Synthesis of 1-(2-naphthalen-2-yl-2-oxo-ethyl)-tetrahydro-thiophenium 5-chloro-4-nitrothiophene-2-sulfonate (NTN)

To a solution of silver 5-chloro-4-nitrothiophene-2-sulfonate (0.456 g, 1.3 mmol) in 25 mL of acetonitrile was added a solution of 1-(2-naphthalen-2-yl-2-oxo-ethyl)-tetrahydro-thiophenium bromide (0.439 g, 1.3 mmol) in 25 mL of acetonitrile and 2 mL of water. The resulting mixture was stirred overnight for 3 days before it was filtered through Celite® and the remaining solid was washed by 50 mL of acetonitrile. The organic solvent was then removed via rotary evaporator and the residue was taken by 100 mL of 2-butanone. The resulting organic solution was then dried over magnesium sulfate, filtered though Celite® and basic aluminum oxide, concentrated via rotary evaporator, dried over vacuum oven to dryness and thus afforded 0.49 g of product at a yield of 75%.
$^1$HNMR, d6-DMSO: 8.73 (d, 0.6 Hz, 1H), 8.15 (d, 8.4 Hz, 1H), 8.12 (d, 8.8 Hz, 1H), 8.07 (d, 8.0 Hz, 1H), 8.01 (dd, 8.4 Hz, 1.6 Hz, 1H), 7.74 (td, 6.8 Hz, 1.2 Hz, 1H), 7.70 (td, 8.0 Hz, 1.2 Hz, 1H), 7.48 (s, 1H), 5.47 (s, 2H), 3.68-3.51 (m, 4H), 2.38-2.18 (brm, 4H). DSC (10° C./min, nitrogen 5 mL/min): Td, 205° C.

Comparison Photoacid Generators

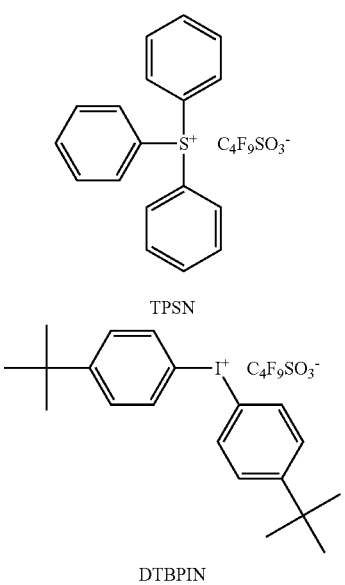

Example 10

Photoresist Formulation 1

5.2959 g of a photoresist polymer consisting of 15 mol % of 2-trifluoromethanesulfonylamino methacrylate, 45 mol % of 2-methyl-2-adamantyl methacrylate and 40 mol % of 5-methacryloyloxy-2,6-norbornanecarbo-γ-lactone (S1) (28.3 wt % solution in PGMEA), 0.3739 g of triphenyl sulfonium nonafluorobutanesulfonate (TPSN) (20.28 wt % solution in PGMEA), 0.4528 g of N-t-Boc-pyrrolidine (1 wt % solution in PGMEA), 10.1472 g of PGMEA and 6.2863 g of cyclohexanone were mixed and rotated overnight, filtered though 0.2 μm PTFE disc to afford formulation 1.

Example 11

Photoresist Formulation 2

5.3081 g of photoresist polymer S1 (28.3 wt % solution in PGMEA), 0.0677 g of TPSTN, 0.4609 g of N-t-Boc-pyrrolidine (1 wt % solution in PGMEA), 10.3710 g of PGMEA and 6.2693 g of cyclohexanone were mixed and rotated overnight, filtered though 0.2 μm PTFE disc to afford formulation S1004.

Example 12

Photoresist Formulation 3

5.3086 g of photoresist polymer S1 (28.3 wt % solution in PGMEA), 0.0747 g of DPTBPSTN, 0.4654 g of N-t-Boc-pyrrolidine (1 wt % solution in PGMEA), 10.4370 g of PGMEA and 6.3010 g of cyclohexanone were mixed and rotated overnight, filtered though 0.2 μm PTFE disc to afford formulation 3.

Example 13

Photoresist Formulation 4

5.3008 g of photoresist polymer S1 (28.3 wt % solution in PGMEA), 0.0848 g of DTBPITN, 0.4545 g of N-t-Boc-pyrrolidine (1 wt % solution in PGMEA), 10.5294 g of PGMEA and 6.3441 g of cyclohexanone were mixed and rotated overnight, filtered though 0.2 μm PTFE disc to afford formulation 4.

Example 14

Photoresist Formulation 5

5.2986 g of photoresist polymer S1 (28.3 wt % solution in PGMEA), 0.0569 g of TPSThio, 0.4640 g of N-t-Boc-pyrrolidine (1 wt % solution in PGMEA), 10.2672 g of PGMEA and 6.2251 g of cyclohexanone were mixed and rotated overnight, filtered though 0.2 μm PTFE disc to afford formulation 5.

Example 15

Photoresist Formulation 6

5.3093 g of photoresist polymer S1 (28.3 wt % solution in PGMEA), 0.0926 g of Di(4-t-butylphenyl) sulfonium nonafluorobutanesulfonate (DTBPIN), 0.4577 g of N-t-Boc-pyrrolidine (1 wt % solution in PGMEA), 10.6040 g of PGMEA and 6.3728 g of cyclohexanone were mixed and rotated overnight, filtered though 0.2 μm PTFE disc to afford formulation 6.

Example 16

Photoresist Formulation 7

5.3031 g of photoresist polymer S1 (28.3 wt % solution in PGMEA), 0.0624 g of BTN, 0.4673 g of N-t-Boc-pyrrolidine (1 wt % solution in PGMEA), 10.3110 g of PGMEA and 6.2423 g of cyclohexanone were mixed and rotated overnight, filtered though 0.2 μm PTFE disc to afford formulation 7.

Example 17

Photoresist Formulation 8

5.3029 g of photoresist polymer S1 (28.3 wt % solution in PGMEA), 0.0676 g of NTN, 0.4575 g of N-t-Boc-pyrrolidine (1 wt % solution in PGMEA), 10.3540 g of PGMEA and 6.2668 g of cyclohexanone were mixed and rotated overnight, filtered though 0.2 μm PTFE disc to afford formulation 8.

Example 18

Photoresist Formulation 9

0.7514 g of a photoresist polymer consisting 60 mol % of 2-methyl-acrylic acid-(3,3,3-trifluoro-2-hydroxy-2-trilfluoromethyl-propyl)-bicyclo[2,2,1]hept-2-yl-ester and 40 mol % of 2-methyl-2-adamantyl methacrylate (F1), 0.0171 g of TPSTN, 0.1148 g of N-t-Boc-pyrrolidine (1 wt % solution in PGMEA), 7.0432 g of PGMEA and 3.0522 g of cyclohexanone were mixed and rotated overnight, filtered though 0.2 μm PTFE disc to afford formulation 9.

Physical Properties

Thin solid films were prepared by spin-coating photoresist formulations over 5 inch silicon wafers at the spin rate of 1500 rpm for 30 seconds. The resulting films were soft baked at 110° C. for 60 seconds. The thickness, n and k were measured by VASE ellipsometry, OD values were calculated from k.

For lithographic evaluation, the prepared photoresists formulation was spin-coated for 30 seconds onto an antireflective coating material (AR 40, Rohm-Haas) layer applied on silicon wafers. The resist film was baked at 110° C. for 60 seconds on a vacuum hotplate for 60 seconds. The wafers were then exposed to 193 nm radiation (ASML, scanner, 0.75 NA). The exposure pattern was an array of lines and spaces of various dimensions down to 90 nm. The exposed wafer was then post-exposure baked on a vacuum hot plate at 120° C. for 90 seconds. The wafers were puddle developed by 0.263 N TMAH developer for 60 seconds. The resulting patterns of the photoresist imaging layers were examined by scanning electron microscopy (SEM). The photospeed results were obtained the images of 90 nm line in 245 nm pitch.

TABLE 1

Physical properties of photoresist composite thin films containing hetero-aromatic PAGs.

| Formulation | PAG | Thickness (nm) | n (193 nm) | k | OD (μm$^{-1}$) | Photospeed (mJ) |
|---|---|---|---|---|---|---|
| 1 | TPSN | 215.64 | 1.6993 | 0.034978 | 0.99 | 14.5 |
| 2 | TPSTN | 207.17 | 1.7003 | 0.033035 | 0.93 | 8 |
| 3 | DPTBPSTN | 208.78 | 1.6965 | 0.034486 | 0.98 | 30 |
| 4 | DTBPITN | 215.46 | 1.7008 | 0.031285 | 0.88 | 45.5 |
| 5 | TPSThio | 214.10 | 1.7014 | 0.031855 | 0.90 | NA |
| 6 | DPTBPIN | 215.15 | 1.7007 | 0.030923 | 0.87 | 18.8 |
| 7 | BIN | 221.48 | 1.6772 | 0.021606 | 0.61 | |
| 8 | NTN | 225.15 | 1.6851 | 0.019420 | 0.55 | |

Leaching Tests:

Resist formulation 2 was spin-coated on bare silicon wafer at 1500 rpm for 30 seconds and baked at 110° C. on a vacuum hotplate for 60 seconds. Topcoat TCX-041 was spin-coated onto the resulting resist film at 1500 rpm for 30 seconds and soft baked on a vacuum hotplate at 90° C. for 60 seconds. The resulting wafer was evaluated by water leaching test. 0.231 ng/mL of PAG TPSTN in water bleaching sample was found by HPLC-MS test.

What is claimed is:

1. A fluorine-free photoacid generator, said photoacid generator comprising an onium cationic component and an anionic component having the structure:

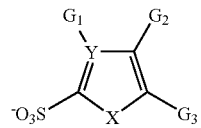

wherein:

X is S,

R is selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;

Y is C;

each of $G_1$-$G_3$ is selected from the group consisting of R and an electron withdrawing moiety, and at least one of $G_1$-$G_3$ is an electron withdrawing moiety selected from the group consisting of CN, NO, $NO_2$, Cl, Br, I, $SO_2Me$ and CHO.

2. The photoacid generator of claim 1 wherein at least two of $G_1$-$G_3$ are electron withdrawing moieties.

3. The photoacid generator of claim 1 wherein said onium cationic component is selected from the group consisting of sulfonium cations and iodonium cations.

4. The photoacid generator of claim 3 wherein said onium cationic component comprises an aromatic moiety.

5. The photoacid generator of claim 4 wherein said onium cationic component has a structure selected from the group consisting of

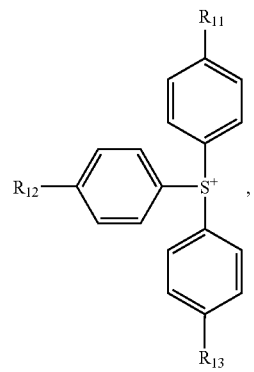

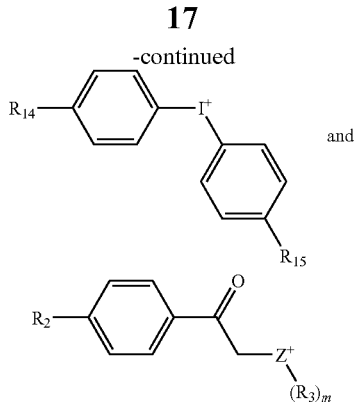

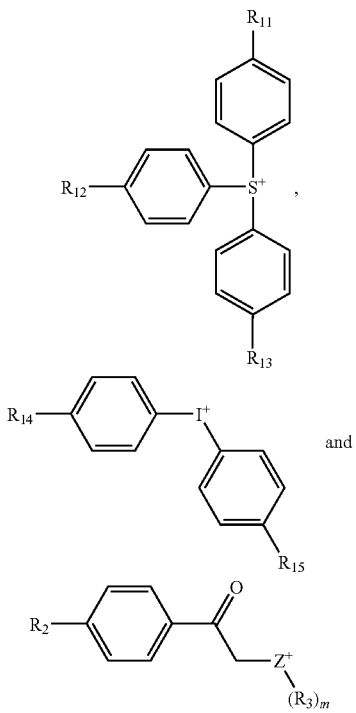

where:
Z is either sulfur or iodine;
m is 1 where Z is iodine and 2 where Z is sulfur;
each $R_{11}, R_{12}, R_{13}, R_{14}, R_{15}$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;
each $R_2$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl; and
each $R_3$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl.

6. A chemically amplified photoresist composition comprising:
(a) an acid sensitive imaging polymer, and
(b) a fluorine-free photoacid generator comprising an onium cationic component and an anionic component having the structure:

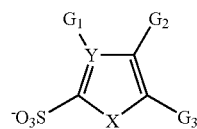

wherein:
X is S,
R is selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;
Y is C;
each of $G_1$-$G_3$ is selected from the group consisting of R and an electron withdrawing moiety, and
at least one of $G_1$-$G_3$ is an electron withdrawing moiety selected from the group consisting of CN, NO, $NO_2$, Cl, Br, I, $SO_2Me$, and CHO.

7. The composition of claim 6 wherein at least two of $G_1$-$G_3$ are electron withdrawing moieties.

8. The composition of claim 6 wherein said onium cationic component is selected from the group consisting of sulfonium cations and iodonium cations.

9. The composition of claim 8 wherein said onium cationic component comprises an aromatic moiety.

10. The composition of claim 9 wherein said onium cationic component has a structure selected from the group consisting of where:
Z is either sulfur or iodine;
m is 1 where Z is iodine and 2 where Z is sulfur;
each $R_{11}, R_{12}, R_{13}, R_{14}, R_{15}$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;
each $R_2$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl; and
each $R_3$ is independently selected from the group consisting of each R is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl.

11. The composition of claim 6 wherein said imaging polymer comprises a lactone moiety.

12. A method of forming a patterned material feature on a substrate, said method comprising:
(a) providing a material surface on a substrate,
(b) forming a photoresist layer over said material surface, said photoresist comprising:
(i) an acid sensitive imaging polymer and
(ii) a fluorine-free photoacid generator comprising an onium cationic component and an anionic component having the structure:

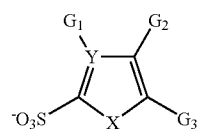

wherein:

X is S,

R is selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;

Y is C;

each of $G_1$-$G_3$ is selected from the group consisting of R and an electron withdrawing moiety, (c) patternwise exposing said photoresist layer to radiation thereby creating a pattern of radiation-exposed regions in said photoresist layer, (d) selectively removing portions of said photoresist layer to expose portions of said material surface, and (e) etching or ion implanting said exposed portions of said material, thereby forming said patterned material feature, wherein at least one of the $G_1$-$G_3$ moieties is an electron withdrawing moiety selected from the group consisting of CN, NO, $NO_2$, Cl, Br, I, $SO_2Me$, and CHO.

13. The method of claim 12 wherein said radiation is provided by an ArF laser.

14. The method of claim 12 wherein said onium cationic component is selected from the group consisting of sulfonium cations and iodonium cations.

15. The method of claim 14 wherein said onium cationic component comprises an aromatic moiety.

16. The method of claim 15 wherein said onium cationic component has a structure selected from the group consisting of

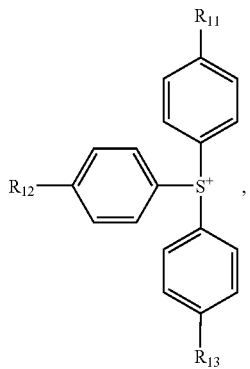

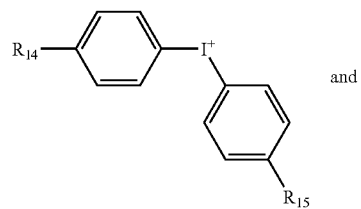

and

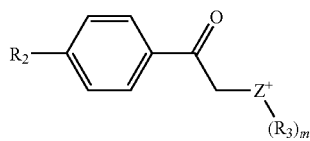

where:

Z is either sulfur or iodine;

m is 1 where Z is iodine and 2 where Z is sulfur;

each $R_{11}$, $R_{12}$, $R_{13}$, $R_{14}$, $R_{15}$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl;

each $R_2$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl; and each $R_3$ is independently selected from the group consisting of H; linear, branched, tertiary, or cyclic alkyl; linear, branched, tertiary or cyclic alkoxyl; unsubstituted and substituted phenyl; unsubstituted and substituted naphthyl; or unsubstituted and substituted fluorenyl.

17. The method of claim 12 wherein said imaging polymer comprises a lactone moiety.

* * * * *